(12) United States Patent
Kane (10) Patent No.: US 8,313,710 B2
(45) Date of Patent: *Nov. 20, 2012

(54) MULTILAYERED OPTICAL SENSING PATCH AND RETAINING PLUG THEREFOR

(75) Inventor: James A Kane, Needham Heights, MA (US)

(73) Assignee: Polestar Technologies, Inc., Needham Heights, MA (US)

( * ) Notice: Subject to any disclaimer, the term of this patent is extended or adjusted under 35 U.S.C. 154(b) by 433 days.

This patent is subject to a terminal disclaimer.

(21) Appl. No.: 12/152,746

(22) Filed: May 16, 2008

(65) Prior Publication Data

US 2008/0286155 A1    Nov. 20, 2008

Related U.S. Application Data

(63) Continuation-in-part of application No. 11/803,901, filed on May 15, 2007, now abandoned.

(51) Int. Cl.
    *G01N 33/52*    (2006.01)
(52) U.S. Cl. ........ 422/421; 422/400; 422/401; 422/420; 422/422; 422/423; 422/424; 422/425; 422/426; 422/427; 422/428; 422/429; 422/68.1; 422/82.05; 422/82.06; 436/164; 436/169; 436/170; 435/13; 435/283.1; 435/287.1; 435/287.7; 435/287.8; 435/287.9; 435/288.7
(58) Field of Classification Search ............. 422/55, 422/56, 57, 400, 401, 420, 421, 422, 423, 422/424, 425, 426, 427, 428, 429, 68.1, 82.05, 422/82.06; 436/169, 164, 170; 435/13, 283.1, 435/287.1, 287.7, 287.8, 287.9, 288.7
See application file for complete search history.

(56) References Cited

U.S. PATENT DOCUMENTS

| | | | | |
|---|---|---|---|---|
| 4,935,346 A | * | 6/1990 | Phillips et al. | 435/14 |
| 5,037,615 A | * | 8/1991 | Kane | 422/82.08 |
| 5,273,716 A | * | 12/1993 | Northrup et al. | 422/82.07 |
| 5,296,192 A | * | 3/1994 | Carroll et al. | 422/56 |
| 5,306,623 A | * | 4/1994 | Kiser et al. | 435/14 |

OTHER PUBLICATIONS

Lee et al , "Thin Film Optical Sensors Employing Polyelectrolyte Assembly", Langmuir 2000, 16, 10482-10489.*

* cited by examiner

Primary Examiner — Dennis M White
(74) Attorney, Agent, or Firm — Burns & Levinson LLP; Orlando Lopez (57) ABSTRACT

A multilayered optical sensing patch, for the measurement of conditions, such as pH, oxygen level, etc, within containers, is provided. The multilayered optical sensing patch of the present invention is comprised of a heat sealable polymer substrate layer, and a polymeric sensing membrane later attached thereto. The polymer sensing membrane layer is formed of a porous polymer support membrane, and an optical sensing composition (comprising a reactive indicator) covalently bonded thereto. The heat sealable polymer substrate layer is capable of being securely bonded to the inner layer of bioreactor bags, as well as the porous polymer support substrate layer. Further, the porous polymer support membrane layer provides a firm supporting structure for the polymeric sensing layer, thereby protecting the optical sensing composition disposed therein from degradation/damage.

7 Claims, 5 Drawing Sheets

MULTILAYERED OPTICAL SENSING PATCH AND RETAINING PLUG THEREFOR

The present application is a CIP (continuation-in-part) patent application of parent copending U.S. patent application Ser. No. 11/803,901, filed May 15, 2007, now pending, the contents of which are incorporated herein by reference.

FIELD OF THE INVENTION

The present invention provides a multilayered optical sensing patch, for the measurement of conditions, such as pH, oxygen level, etc, within containers, as well as a retaining plug for securing same to a container of interest. In particular, a multilayered optical sensing patch is provided, having a heat sealable polymer substrate layer, and a polymeric sensing membrane attached to the heat sealable polymer substrate layer, the polymeric sensing membrane comprised of a porous polymer support membrane having an optical sensing composition covalently bonded thereto. In addition, a retaining plug, capable of retaining the optical sensing patch in contact with a solution to be measured, and of being heat welded to a container, is provided.

BACKGROUND OF THE INVENTION

Optical sensing patches have conventionally been provided for the detection/measurement of oxygen, carbon dioxide and pH. Multilayered oxygen and pH sensing patches are currently sold which, for example, have either a glass or polyester substrate film, upon which is deposited a layer of silicone rubber impregnated with a fluorescent indicator that undergoes oxygen dependent quenching resulting in a reduction in the fluorescence lifetime and emission intensity. Conventional pH sensing patches also use polyester substrates, on which is deposited a hydrogel layer containing a fluorescent pH sensitive indicator.

Some conventional patches are affixed to the inner wall of the container of interest by use of an adhesive that is applied to the patch substrate by the end user. Other conventional oxygen and pH sensing patches have a multilayer design, with a polyester substrate. However, these patches are supplied with an adhesive layer in a peel and stick type format.

Most conventional optical sensing patches disadvantageously require adhesives to attach the sensing film. This use of adhesives creates the potential for delamination when used with polyolefin surfaces (e.g., polypropylene and polyethylene), such as are commonly used as the inner layer of disposable bag-type bioreactors. The polyolefin inner layers of these disposable bag-type bioreactors are important because they impart high biocompatibility and an ability to use heat sealing in the construction of the bag. Further, polyolefins are considered low energy surfaces which lack chemical functional groups that might normally be used to covalently couple with an adhesive layer. For these reasons, cyanoacrylate, epoxy, polyurethane, silicone, and most acrylic adhesives do not adhere to polyolefins.

Conventional optical sensing patches, which utilize direct deposition of the pH sensing hydrogel layer onto a polyester substrate film, are also easily damaged. In particular, while the polyester substrate does provide the hydrogels with a degree of mechanical support, it fails to protect against damage due to handling or abrasives in the solutions to be monitored.

In view of the above-described disadvantages encountered with conventional optical sensing patches, it is an object of the present invention to provide an optical sensing patch capable of effectively bonding to the inner layer of bag bioreactors.

It is a further object of the present invention to provide an optical sensing patch which is durable and resistant to damage. In particular, it is an object of the present invention to provide an optical sensing patch which provides significantly enhanced protection against damage to the sensing composite, by providing a robust scaffold upon which the sensing composite can be deployed.

SUMMARY OF THE INVENTION

In order to achieve the above mentioned objects of the present invention, the present inventor earnestly endeavored to provide an multilayered optical sensing patch capable of being bonded to the inner layer of bioreactor bags, while also being capable of securing, in a protective manner, the optical sensing composition of interest. Accordingly, in a first embodiment of the present invention, a multilayered optical sensing patch comprising:

(a) a heat sealable polymer substrate layer; and
(b) a polymeric sensing membrane layer attached to said heat sealable polymer substrate layer, said polymeric sensing membrane layer comprised of:
  (i) a porous polymer support membrane layer having a plurality of pores disposed therein; and
  (ii) an optical sensing composition comprising a reactive indicator capable of covalently bonding to chemical groups on the porous polymer support membrane.

In a second embodiment of the present invention, the multilayered optical sensing patch of the first embodiment above is provided, wherein the reactive indicator of the optical sensing composition comprises a fluorescent or colorimetric sensing composition for the detection or measurement of oxygen, pH, carbon dioxide, ammonia, alkali and alkaline-earth metal ions, nutrients such as glucose, or metabolites such as lactate, acetate.

In a third embodiment of the present invention, the multilayered optical sensing patch of the first embodiment above is provided, wherein the reactive indicator comprises one or more of isothiocyanates, isocyanates, succinimidyl esters, sulfonyl chloride, and vinyl sulfoesters.

In a fourth embodiment of the present invention, the multilayered optical sensing patch of the third embodiment above is provided, wherein the reactive indicator is one or more of 8-hydroxypyrene-1,3,6-trisulfonyl chloride, fluorescein isothiocyanate, Oregon Green® isothiocyanate, Oregon Green® carboxylic acid, succinimidyl ester (5 or 6 isomer), 5-(and 6)-carboxy SNAFL®-1, succinimidyl ester, and 5-(and 6)-carboxy SNAFL®-1, succinimidyl ester.

In a fifth embodiment of the present invention, the multilayered optical sensing patch of the first embodiment above is provided, wherein the heat sealable polymer substrate layer is comprised of one or more of a polyether, polyamide, polyvinyl or polyolefin.

In a sixth embodiment of the present invention, the multilayered optical sensing patch of the first embodiment above is provided, wherein the heat sealable polymer substrate has an optical transparency of 50% or greater over the spectral range of interest.

In a seventh embodiment of the present invention, the multilayered optical sensing patch of the first embodiment above is provided, wherein the porous polymer support membrane is comprised of nylon, polyester, cellulous acetate, or nitrocellulous.

In an eighth embodiment of the present invention, the multilayered optical sensing patch of the first embodiment above is provided, wherein the porous polymer support membrane has a pore size of from about 0.1 to about 20 μm.

In a ninth embodiment of the present invention, the multilayered optical sensing patch of the first embodiment above is provided, wherein the porous polymer support membrane has an onset melt temperature of 200 degrees centigrade or greater.

In a tenth embodiment of the present invention, the multilayered optical sensing patch of the first embodiment above is provided, wherein the porous polymer support membrane is attached to the heat sealable polymer membrane at an interpenetrating interfacial region, said interfacial region being formed by percolation of the heat sealable polymer membrane into the pores of the porous polymer support membrane during heating.

In an eleventh embodiment of the present invention, the multilayered optical sensing patch of the first through third embodiments above is provided, wherein the optical sensing composition is directly chemically bonded to the porous polymer support membrane, by covalently bonding of the reactive indicator directly to active (free) amines or hydroxyl groups on the porous polymer support membrane.

In a twelfth embodiment of the present invention, the multilayered optical sensing patch of the first embodiment above is provided, wherein the heat sealable polymer substrate is polyethylene, the porous polymer support membrane is a microporous nylon, and the optical sensing composition is comprised of particles, said particles being covalently bonded to microporous nylon.

In a thirteenth embodiment of the present invention, a method of manufacturing the multilayered optical sensing patch of the first embodiment above is provided, comprising the steps of:

(a) soaking the porous polymer support membrane in a pH buffer composition, dimethyl formamide, or triethylamine in water solution;

(b) placing the porous polymer support membrane in a solution comprising the reactive indicator, and allowing the porous polymer support membrane to soak in the solution for a time period sufficient to allow the reactive indicator to covalently bond to the free amines on the porous polymer support membrane;

(d) removing any unbound reactive indicator from the polymer sensing membrane layer by decanting the solution and/or rinsing the solution from the porous polymer support membrane; and (e) laminating the heat sealable polymer substrate film to the porous polymer support membrane layer, having pores therein, using a combination of heat and pressure.

In a fourteenth embodiment of the present invention, an optical sensing patch retaining plug is provided comprising:

a plug body having a plug face;

an optical sensing patch in communication with the plug face; and a fiber optic insertion channel disposed within said plug body, said fiber optic insertion channel being disposed adjacent to the optical sensing patch, wherein at least a portion of the plug face not in communication with the optical sensing patch may be welded to a bioreactor bag or other container of interest.

In a fifteenth embodiment of the present invention, the optical sensing patch retaining plug of the fourteenth embodiment is provided, wherein the plug body is comprised of heat sealable material.

In a sixteenth embodiment of the present invention, the optical sensing patch retaining plug of the fourteenth embodiment is provided, wherein the heat sealable material is comprised of one or more of polypropylene, low density polyethylene, linear low density polyethylene, ethyl vinyl acetate, hydrolyzed ethylene vinyl acetate, low vinyl acetate ethylene-vinyl acetate copolymer, polyvinylidene fluoride, styrene butadiene copolymers, ionomers, acid copolymers, thermoplastic elastomers, and plastomers.

In a seventeenth embodiment of the present invention, the optical sensing patch retaining plug of the fourteenth embodiment is provided, wherein the fiber optic insertion channel comprises a means for securely retaining a fiber optic device therein.

In an eighteenth embodiment of the present invention, the optical sensing patch retaining plug of the seventeenth embodiment is provided, wherein the means for securely retaining a fiber optic device comprises threaded members, compression fit retaining devices and/or adhesives.

DETAILED DESCRIPTION OF THE INVENTION

Figure 1:
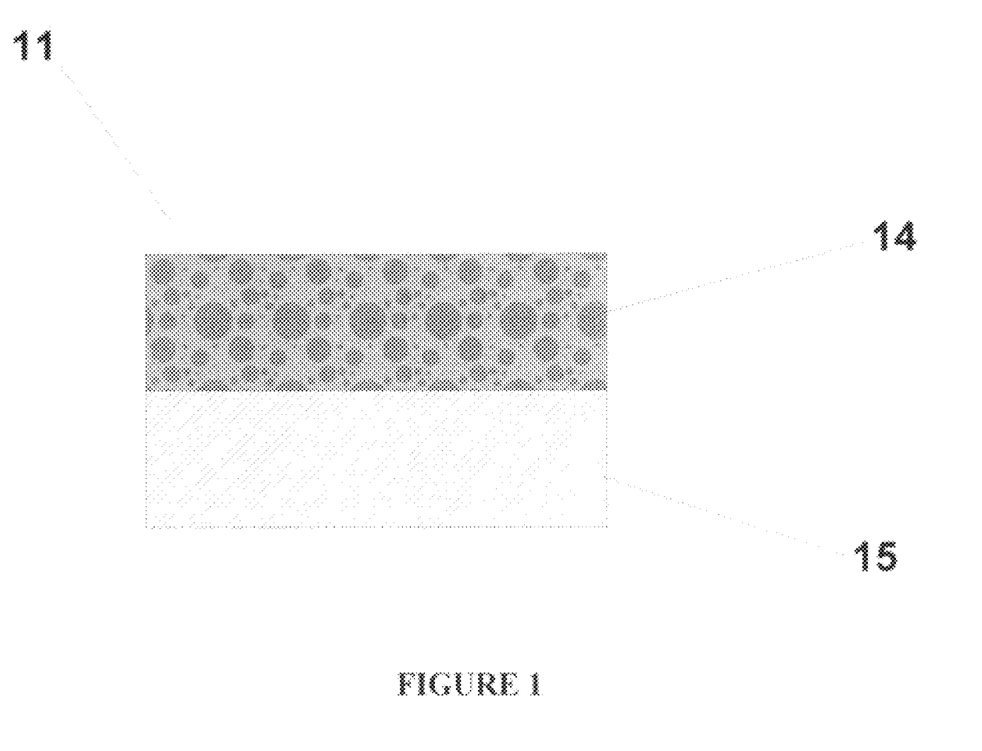
FIG. 1 is a cross-sectional drawing of the multilayered optical sensing patch of with covalently attached indicator of the present invention.

The present invention provides multilayered optical sensing patches having three basic polymeric layers. In particular, as illustrated in FIG. 1, the multilayered optical sensing patch 11 of the present invention includes a heat sealable polymer substrate layer 15, and a polymeric sensing membrane 14 attached to the heat sealable polymer substrate layer 15. The polymeric sensing membrane 14 is formed of a porous polymer support membrane layer having one or more optical sensing compositions covalently bonded thereto, and coating the pores thereof. The heat sealable polymer substrate layer 15 allows the multilayered optical sensing patch 11 of the present invention to be securely adhered to the inner layer of bioreactor containers/bags.

Further, the polymeric sensing membrane layer 14 of the present invention significantly enhances protection against damage to the optical sensing composition (which is bonded to the polymeric sensing membrane layer 14) by providing a robust scaffold upon which the optical sensing composition can be deployed. Specifically, covalent bonding of the optical sensing composition to the polymeric sensing membrane 14 moves the more fragile optical sensing composition(s) away from the surface where abrasive contact can occur.

The heat sealable polymer substrate layer 15 may be comprised of a polyether, polyamide, or polyolefin. The heat sealable polymer substrate layer 15 should have good optical transparency, to allow for optical measurement therethrough. In particular, an optical transparency of 50% or greater over the spectral range of interest is preferred. Further, the heat sealable layer polymer substrate layer 15 should have a low processing temperature, to enable it to heat seal with the porous polymer support membrane of the polymeric sensing membrane layer 5 without damaging the support membrane layer. In particular, a processing temperature of 180 degrees centigrade or less is preferred.

The polymeric sensing membrane layer 14 is heat sealed to the heat sealable polymer substrate layer 15. In particular, the heat sealable layer 15 is disposed adjacent the polymeric sensing membrane layer 14, and both layers are heated to a temperature higher than the onset melting point of the heat sealable layer 15, but lower than the melt temperature of the polymeric sensing membrane layer 14. During heating, a portion of the molten heat sealable layer 15 percolates into the porous polymer support layer of the polymeric sensing membrane layer 5 such that, upon cooling, a strong mechanical bond is formed between the two layers. The porous polymer support membrane may be comprised of nylon, polyester, cellulous acetate, or nitrocellulous.

In a preferred embodiment, the porous polymer support membrane is comprised of nylon. The porous polymer support membrane has a plurality of pores formed therein, each pore preferably having a pore size of between about 0.1 and about 20 μm, so as to be capable of allowing the polymeric sensing membrane layer 7 to be immobilized therein.

Further, as described above, the porous polymer support membrane layer of the polymeric sensing layer 14 should have a high melt and/or decomposition temperature. In particular, it is preferred that the melt temperature of the porous polymer support membrane be higher than that of the heat sealable layer 15, so as to allow the porous polymer support membrane to withstand the heat sealing process described above. It is preferred that the porous polymer support membrane have an onset melt temperature of 200 degrees centigrade or greater.

In an alternative embodiment, the porous polymer support membrane of the polymeric sensing membrane layer 14 is formed of woven plastic (i.e., nylon). In such an alternative embodiment, such support structure could be used in place of the macro-porous polymer support membrane layer described above.

The polymeric sensing membrane layer 14 is a vehicle for immobilizing the indicator chemistry (i.e., the optical sensing composition) used for sensing. In particular, the reactive indicator is directly chemically attached to the porous polymer membrane. Preferably, the reactive indicator is covalently bonded to the porous polymer support membrane 14. By providing a means of chemical attachment, the need for an indictor binding polymer is eliminated. Further, by directly attaching the reactive indicator to the porous polymer membrane, no reduction in the pore volume of the porous membrane occurs. This provides a faster response time than is observed with sensing patches fabricated with direct attachment indicators.

As mentioned above, the polymeric sensing membrane layer 14 contains one or more optical sensing compositions, which comprise reactive indicators, covalently bonded to the surface of the porous polymer support membrane layer. The reactive indicators of the optical sensing composition generally comprise one or more of a fluorescent or calorimetric sensing composition for the detection or measurement of oxygen, pH, carbon dioxide, ammonia, alkali and alkaline-earth metal ions, nutrients such as glucose, or metabolites such as lactate, acetate.

Preferably, the reactive indicators are comprised of one or more of isothiocyanates, isocyanates, succinimidyl esters, sulfonyl chloride, and vinyl sulfoesters. Most preferably, the reactive indicators are one or more of 8-hydroxypyrene-1,3,6-trisulfonyl chloride, fluorescein isothiocyanate, Oregon Green® isothiocyanate, Oregon Green® carboxylic acid, succinimidyl ester (5 or 6 isomer), 5-(and 6)-carboxy SNAFL®-1, succinimidyl ester, and 5-(and 6)-carboxy SNAFL®-1, succinimidyl ester. Fluorescein, Oregon Green®, and succinimidyl ester covalent attach to the porous polymer support membrane by formation of an amide bond. Fluorescein isothiocyanate (FITC) covalent attaches to the porous polymer support through a thiourea linkage. 8-hydroxypyrene trisulfonyl chloride covalent attaches to the porous polymer support membrane through a sulfonamide linkage.

The polymeric sensing membrane layer 14, having the reactive indicator(s) covalently bonded thereto, is attached to the heat sealable layer 15 by the formation of an interpenetrating interfacial region, formed by percolation of the material of the heat sealable layer 15 into the polymeric sensing membrane layer 14 during heating.

Examples of porous membranes used to construct the multilayered optical sensing patches of the present invention include those from GE OSMONICS®. In a preferred embodiment of the present invention, the porous membrane is comprised of GE Osmonics® Magna® nylon, having varying porosity.

Experiments conducted by the present inventor have shown that the optical sensing composition (comprising the reactive indicator) can be covalently bonded to the porous polymer support membrane layer before or after heat sealing thereof with the polyolefin comprising the heat sealable layer 15. Thus, it has been unexpectedly discovered that the polymeric sensing membrane layer 14, containing the optical sensing composition, can be heat sealed directly to the films used to construct bag-type bioreactors, or via a polyolefin layer heat sealed prior to coupling with bag films. It has been found that each approach yields a strong mechanical bond between the sensing film and the bag film.

In an alternative embodiment of the present invention, a multilayered fluorescence sensing film is provided, which combines a porous sensing layer support element and a transparent substrate layer, using a thin layer of adhesive, rather than heat sealing, to bond the two films together. In particular, sensing films have been made with both stainless steel and nylon mesh. However, woven mesh tends to yield sensing layers that are thicker than what are possible with the macro-porous membranes described above, which results in longer response times. The woven mesh also fails to provide as much protection against abrasive damage to the polymeric sensing membrane layer as the porous polymer substrate membrane layer described above.

In order to retain the optical sensing patch of the present invention, as described above, securely against a bioreactor bag or other container of interest, the present inventor has developed an optical sensing patch retaining plug. In particular, this optical sensing patch retaining plug allows the optical sensing patch of the present invention to come into contact with the solution of interest, via a hole formed in the wall of the bioreactor bag or container of interest, to which the retaining plug is securely attached. The retaining plug is heat welded to the bioreactor bag or container of interest around the periphery of the plug face, thereby allowing the optical sensing patch to come into direct contact with the contents of the bioreactor bag, while simultaneously allowing the optical sensing patch to be illuminated by a fiber optic device, emissions thereof measured, and provide an airtight seal.

Figure 2:
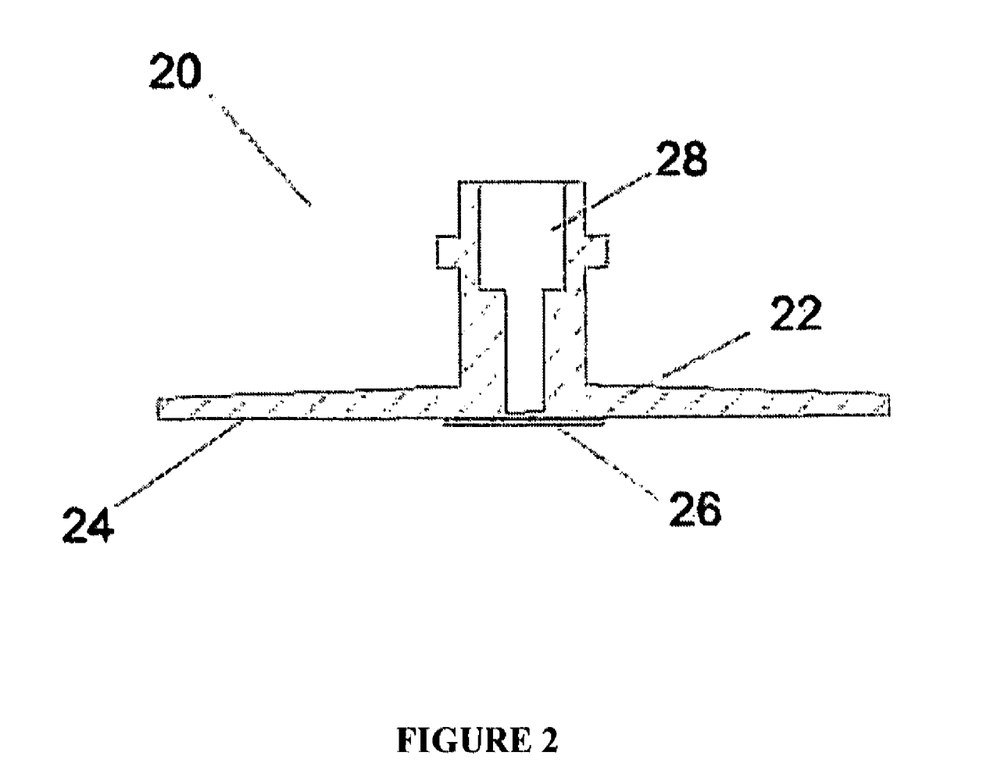
FIG. 2 is a cross sectional view of the optical sensing patch retaining plug of the present invention, having the multilayered optical sensing patch of the present invention attached thereto, which is capable of retaining a fiber optic device adjacent to the optical sensing patch.

Specifically, as illustrated in FIG. 2, an optical sensing patch retaining plug 20 is provided, comprised of a plug body 22. The plug body 22 has a plug face 24 formed continuously therewith. In a preferred embodiment, the plug body 22 is comprised of heat sealable material, enabling heat welding thereof to a bioreactor bag or other container with which an optical sensing patch may be used. Most preferably, the plug body 22 is comprised of one or more of polypropylene, low density polyethylene, linear low density polyethylene, ethyl vinyl acetate, hydrolyzed ethylene vinyl acetate, low vinyl acetate ethylene-vinyl acetate copolymer, polyvinylidene fluoride, styrene butadiene copolymers, ionomers, acid copolymers, thermoplastic elastomers, and plastomers. These material are capable of formed a strong weld to other heat sealable materials, which bioreactors bags, etc., are usually formed of.

An optical sensing patch 26 is disposed adjacent the plug face 24. The optical sensing patch retaining may be a conventional optical sensing patch. Preferably, the optical sensing patch 26 is the optical sensing patch of the present invention as described above.

Disposed within the plug body 22 is a fiber optic insertion channel 28. The fiber optic insertion channel 28 is defined by the material comprising the plug body 22. Importantly, the fiber optic insertion channel 28 is disposed within the plug body 22 adjacent to the area on the plug body 22 where the optical sensing patch 26 is attached/disposed adjacent to, so that the fiber optic may emit light upon the optical sensing patch 26. This may be achieved by forming the fiber optic insertion channel 28 completely through the plug body 22.

However, preferably, a small wall of material forming the plug body 22 is disposed between the fiber optic insertion channel 28 and the area on the plug body 22 where the optical sensing patch 26 is attached/disposed adjacent to. In such a preferred embodiment, the plug body 22 is formed of a material having an optical transparency sufficient to allow the fiber optic device (not illustrated) disposed within the fiber optic insertion channel 28 to adequately illuminate the optical sensing patch 26

The fiber optic insertion channel 28 comprises a means for securedly retaining a fiber optic device therein. For example, threaded members may be formed in the material defining the fiber optic channel 28, so as to allow a fiber optic device to be screwed therein. Or, a compression fit retaining device may be disposed within the channel 28, so as to allow the fiber optic device to be securedly held within the channel 28. Alternatively, the geometry of the channel 28 may be configured so as to provide a secure fit for the fiber optic device, or the fiber optic device may be secured within the channel 28 using one or more adhesive compositions.

Methods of Manufacture of the Optical Sensing Patch:

In addition to a multilayered optical sensing patch, the present invention provides a method of manufacturing the multilayered optical sensing patch of the present invention. In particular, the method of the present invention includes, in a first step, soaking the porous polymer support membrane in a pH buffer composition, dimethyl formamide, or triethylamine in water solution. Then, in a second step, the porous polymer support membrane is placed in a solution comprising the reactive indicator. The porous polymer support membrane is allowed to soak in the solution for a time period sufficient to allow the reactive indicator to covalently bond to the free amines present on the surface of the porous polymer support membrane.

In a third step, unbound reactive indicator molecules are removed from the polymer sensing membrane layer by decanting the solution and/or rinsing the solution from the porous polymer support membrane. Lastly, the heat sealable polymer substrate film is laminated to the porous polymer support membrane layer, having pores therein, using a combination of heat and pressure.

Representative examples of the method described above are provided below as follows:

AQUEOUS PREPARATION EXAMPLE

A GE Osmonics® Magna® nylon film is soaked in pH 8 buffer for about 30 minutes, so as to provide a presoaked nylon film. The presoaked nylon film (having a area of ~100 $cm^2$) is then immersed in a dye solution containing ~4 mg Oregon Green® 488 carboxylic acid, succinimidyl ester, or fluorescein 5-EX succinimidyl ester, dissolved in 100 mL of pH 8 phosphate buffer (0.1M KH2PO4+0.1N NaOH→pH 8). The nylon film is then allowed to react overnight, away from light, though surface primary amino groups. The dye solution is then decanted, and the film rinsed several times in deionized water, thereby providing a polymeric sensing membrane layer.

NON-AQUEOUS PREPARATION EXAMPLE

A nylon film having an area of about 100 $cm^2$ is soaked in DMF (dimethylformamide) for at least 1 hour prior, to obtain a presoaked nylon film. The presoaked Nylon film (~100 $cm^2$) is then immersed in a dye solution containing about ~4 mg Oregon Green® 488 carboxylic acid, succinimidyl ester, or fluorescein 5-EX succinimidyl ester, or acetylated 8-hydroxypyrene-1,3,6-trisulfonyl chloride dissolved in about 100 mL of DMF. The nylon film is allowed to react with the reactive indicators in the dye solution overnight, while refrigerated and away from light, though surface primary amino group. The film is then allowed to warm to room temperature, and allowed to react for several more hours. The dye solution is then decanted, and the film is rinsed in a small quantity of DMF. The DMF is then decanted, and the film is rinsed in several aliquots of deionized water, thereby providing a polymer sensing membrane layer.

Preparation of Fluorescein Modified pH Sensing Film through Isothiocyanate Functional Group:

Nylon film having an area of ~100 $cm^2$ is soaked in pH 8.5 buffer for at least 30 min prior, to obtain a presoaked nylon film. The presoaked nylon film is then added to a dye solution containing about ~4 mg fluorescein isothiocyanate (FITC) dissolved in about 100 mL pH 8.5 phosphate buffer. The film is then allowed to react with the reactive indicator of the dye solution overnight, away from light, though surface primary amino groups. The dye solution is then decanted, and the film rinsed several times in deionized water, thereby providing a polymer sensing membrane layer.

TEST EXAMPLES #1

A polymeric sensing membrane layer film was prepared using the aqueous preparation method described above, using Oregon Green® 488 carboxylic acid, succinimidyl ester as the reactive indicator. The response of same was then tested, by measuring the Signal Magnitude Ratio (SMR) of the film as a function of solution pH. The SMR is defined as the ratio of fluorescence emission signal magnitudes in the wavelength range 520 nm to 610 nm from the film taken under photo excitation with 435 nm and 490 nm light, i.e., SMR=Signal 490 nm/Signal 435 nm In particular, SMR measurements are made by first measuring the fluorescence signal strength of the sensing film while exciting the film with light whose wavelength is 435 nm, then measuring the signal strength while exciting with light whose wavelength is 490 nm, and finally taking the ratio of the signal strengths observed under the two different excitation conditions. The results of these measurements for the exemplary film prepared as described above are shown in FIG. 3 herein. For the data shown in FIG. 3, both excitation light sources were light emitting diodes (LED). Other light sources and/or filter combinations could be used in place of the LED's. There may also be other combinations of wavelengths that could generate similar responses.

TEST EXAMPLE #2

Figure 4:
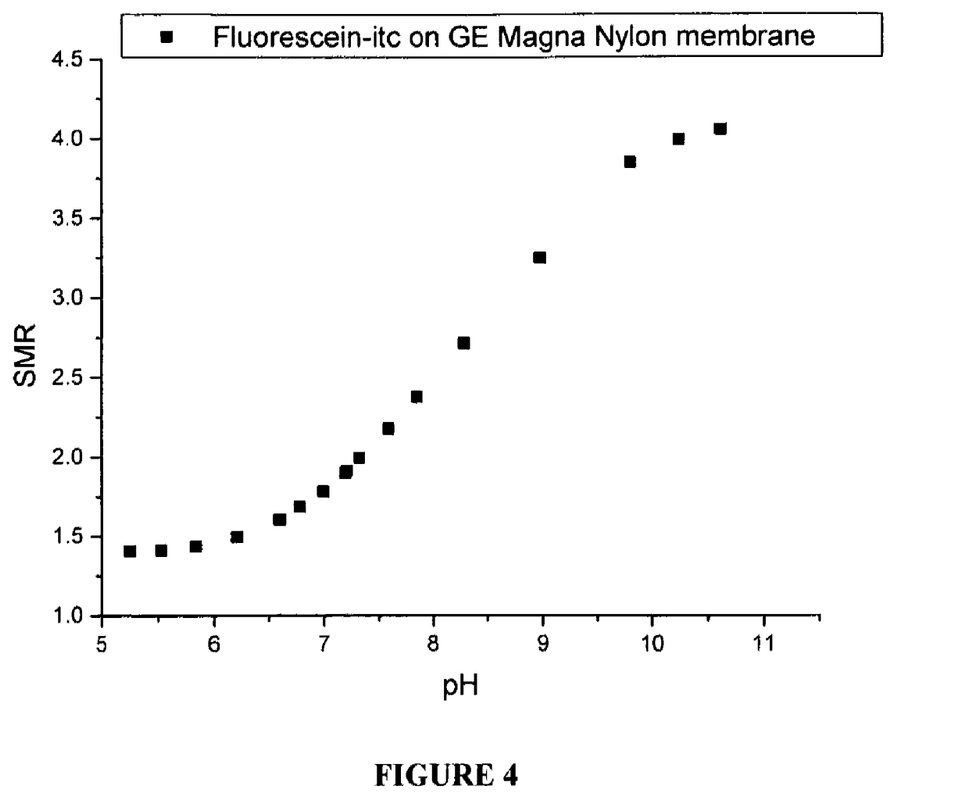
FIG. 4 plot of the response of a fluorescein isothiocyanate as a function of pH.

A fluorescein modified pH sensing membrane layer film was prepared using the isothiocyanate group method disclosed above. The response of same was then tested, by measuring the Signal Magnitude Ratio (SMR) of the film as a function of solution pH, as described above. A plot of the response of a fluorescein isothiocyanate as a function of pH is shown in FIG. 4. These data points were collected by excitation of the film in the same fashion and using the same wavelengths of light as were used to study the Oregon Green® film mentioned above.

TEST EXAMPLE #3

A polymeric sensing membrane film was prepared using the non-aqueous preparation method disclosed above using acetylated 8-hydroxypyrene-1,3,6-trisulfonyl chloride as the reactive indicator. The sensing membrane was soaked overnight in 100 ml DMF containing 4 mg of acetylated 8-hydroxypyrene-1,3,6-trisulfonyl chloride then rinsed with distilled water to remove the DMF and finally soaked pH 9 phosphate buffer to hydrolyze the acetylated hydroxide and unreacted sulfonyl chloride groups to yield covalently attached 8-hydroxypyrene-1,3,6-trisulfonic acid. The response of same was then tested, by measuring the Signal Magnitude Ratio (SMR) of the film as a function of solution pH, as described above. The response of the sensing film containing covalently attached 8-hydroxypyrene-1,3,6-trisulfonic acid HPTS is shown in FIG. 5.

Figure 3:
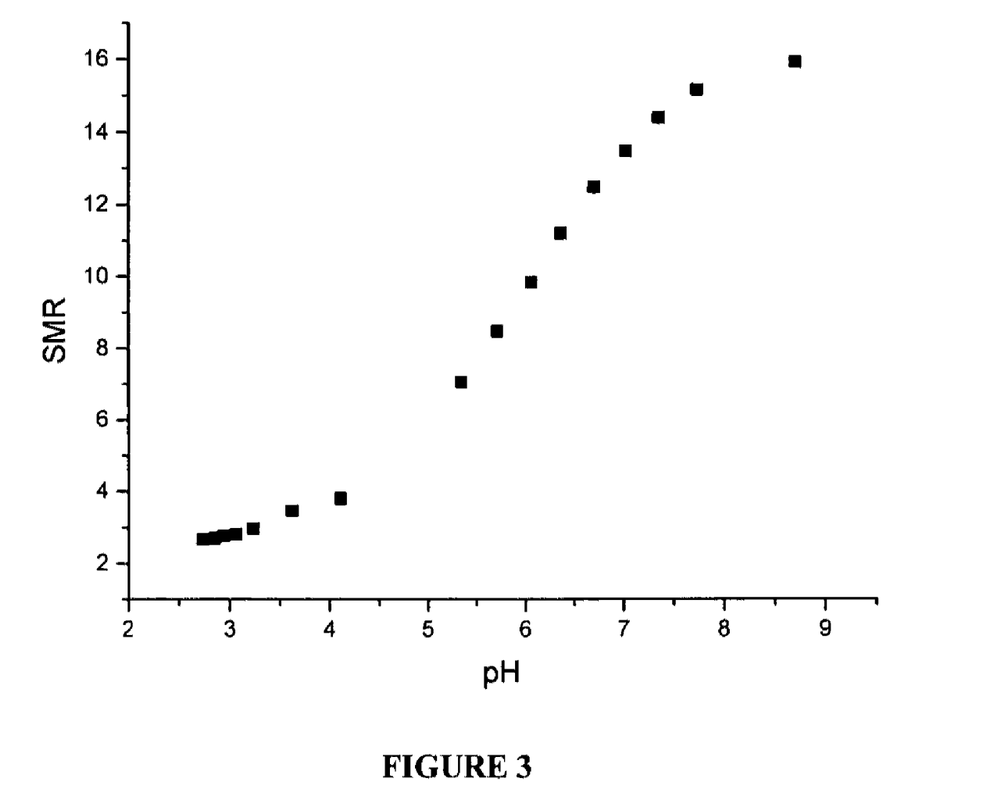
FIG. 3 is a plot shows the Signal Magnitude Ratio (SMR) of the film as a function of solution pH.
Figure 5:
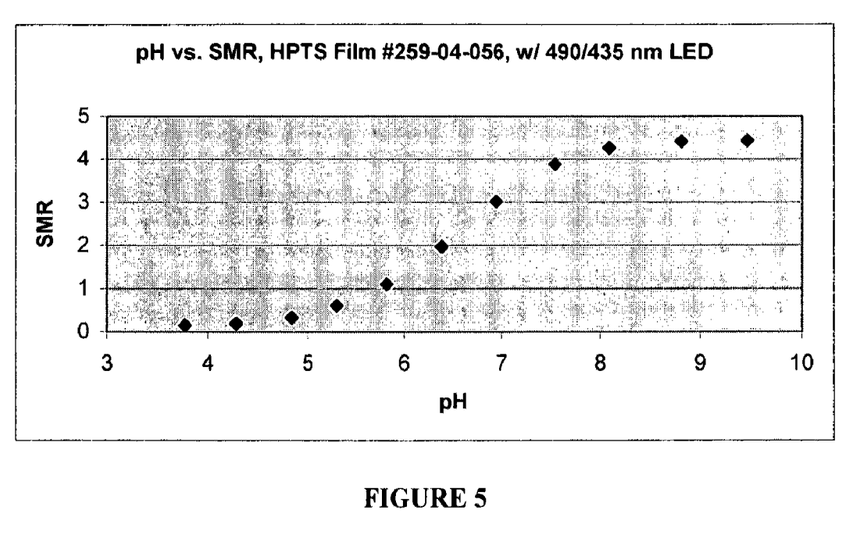
FIG. 5 is a plot illustrating the response of a sensing patch containing covalently attached 8-hydroxypyrene1,3,6-trisulfonic acid (HPTS).

The data illustrated in FIGS. 3-5 illustrate the high pH sensitivity of the sensing patches using the covalently attached indicators. The data also demonstrate the various ranges of response that can be used with the different indicator compounds from fluorescence emission signal ratio measurements as described above.

Although specific embodiments of the present invention have been disclosed herein, those having ordinary skill in the art will understand that changes can be made to the specific embodiments without departing from the spirit and scope of the invention. The scope of the invention is not to be restricted, therefore, to the specific embodiments. Furthermore, it is intended that the appended claims cover any and all such applications, modifications, and embodiments within the scope of the present invention.

What is claimed is:

1. A multilayered optical sensing patch comprising:
   (a) a heat sealable polymer substrate layer comprised of one or more of a polyether, polyamide or polyolefin; and having an optical transparency of 50% or greater over the spectral range of interest and a processing temperature of 180° C. or less;
   (b) a polymeric sensing membrane layer heat sealed to said heat sealable polymer substrate layer said polymeric sensing membrane layer, comprised of:
      (i) a porous polymer support membrane layer having been subjected to a pretreatment, said pretreatment allowing the porous polymer support membrane to withstand a heat sealing process in which both layers are heated to a temperature higher than an onset melting point of the heat polymer substrate sealable layer, but lower than a melt temperature of the polymeric sensing membrane layer; said porous polymer support membrane having a plurality of pores disposed therein; said porous polymer support membrane consisting of nylon, polyester, or nitrocellulose having a pore size of from about 0.1 to about 20 μm and an onset melt temperature of 200° C. or greater,
      (ii) an optical sensing composition comprising a reactive indicator covalently bonded to chemical groups on the porous polymer support membrane, said optical sensing composition comprising a fluorescent or colorimetric sensing composition for the detection or measurement of oxygen, pH, carbon dioxide, ammonia, alkali, and alkaline-earth metal ions, or metabolites; the reactive indicator being covalently bonded to free amines or amino groups on a surface of the porous polymer support membrane.

2. The multilayered optical sensing patch of claim 1, wherein the reactive indicator comprises one or more of isocyanates, succinimidyl esters, sulfonyl chloride, and vinyl sulfoesters.

3. The multilayered optical sensing patch of claim 2, wherein the optical sensing composition is directly chemically bonded to the porous polymer support membrane, by covalently bonding of the reactive indicator directly to active (free) amines on the porous polymer support membrane.

4. The multilayered optical sensing patch of claim 1, wherein the reactive indicator is one or more of acetylated 8-hydroxypyrene-1,3,6-trisulfonyl chloride, fluorescein isothiocyanate, succinimidyl ester (5 or 6 isomer), 5-(and 6)-carboxy SNAFL®-1, and succinimidyl ester.

5. The multilayered optical sensing patch of claim 4, wherein nylon film is soaked in dimethyl formamide, in the absence of light, and then in a dye solution of acetylated 8-hydroxypyrene-1,3,6-trisulfonylchloride, dissolved in dimethyl-formamide.

6. The multilayered optical sensing patch of claim 1, wherein the optical sensing composition is directly chemically bonded to the porous polymer support membrane, which has undergone a pretreatment comprising soaking over night, away from light, said porous polymer membrane of nylon in an aqueous buffer solution pH 8.5 containing dimethyl formamide, and then soaking the nylon membrane in a dye solution containing fluorescein isothiocyanate dissolved in a phosphate buffer having a pH 8.5, to react the reactive indicator with surface primary amine or amino groups.

7. A method of manufacturing the multilayered optical sensing patch of claim 1, comprising the steps of:
   (a) soaking the porous polymer support membrane in a pH buffer composition, dimethyl formamide, or triethylamine in water solution;
   (b) placing the porous polymer support membrane in a solution comprising the reactive indicator, and allowing the porous polymer support membrane to soak in the solution for a time period sufficient to allow the reactive indicator to covalently bond to the free amines on the porous polymer support membrane;
   (d) removing any unbound reactive indicator from the polymer sensing membrane layer by decanting the solution and/or rinsing the solution from the porous polymer support membrane; and
   (e) laminating the heat sealable polymer substrate film to the porous polymer support membrane layer, having pores therein, using a combination of heat and pressure.

* * * * *